United States Patent
Rao et al.

(10) Patent No.: US 7,608,740 B2
(45) Date of Patent: Oct. 27, 2009

(54) METHOD OF SYNTHESIZING KEY INTERMEDIATES FOR THE PRODUCTION OF CAMPTOTHECIN DERIVATIVES

(75) Inventors: Ramakrishna Rao, Andhra Pradesh (IN); Venkata Rama Rao Alla, Andhra Pradesh (IN)

(73) Assignee: Avra Laboratories Pvt. Ltd, Hyderabad (IN)

( * ) Notice: Subject to any disclaimer, the term of this patent is extended or adjusted under 35 U.S.C. 154(b) by 0 days.

(21) Appl. No.: 11/997,688

(22) PCT Filed: Sep. 27, 2005

(86) PCT No.: PCT/IN2005/000326

§ 371 (c)(1), (2), (4) Date: Feb. 1, 2008

(87) PCT Pub. No.: WO2007/015259

PCT Pub. Date: Feb. 8, 2007

(65) Prior Publication Data

US 2008/0221358 A1 Sep. 11, 2008

(30) Foreign Application Priority Data

Aug. 3, 2005 (IN) .................. 1053/CHE/2005

(51) Int. Cl.
*C07C 213/02* (2006.01)
*C07C 205/06* (2006.01)
*C07D 491/12* (2006.01)

(52) U.S. Cl. .................. 564/418; 546/48; 568/306

(58) Field of Classification Search .................. None
See application file for complete search history.

(56) References Cited

U.S. PATENT DOCUMENTS

| 4,031,098 | A | 6/1977 | Sugasawa |
| 4,473,692 | A | 9/1984 | Miyasaka et al. |
| 4,545,880 | A | 10/1985 | Miyasaka et al. |
| 4,604,463 | A | 8/1986 | Miyasaka et al. |
| 5,391,745 | A | 2/1995 | Danishefsky et al. |
| 7,126,000 | B2 | 10/2006 | Ogawa et al. |
| 2004/0106830 | A1 | 6/2004 | Ogawa et al. |

FOREIGN PATENT DOCUMENTS

| EP | 0074256 | 3/1983 |
| EP | 0845464 | 6/1995 |
| EP | 1378505 | 1/2004 |
| EP | 2007015259 | 4/2008 |
| IN | 1053/CHE/2005 | 8/2005 |
| WO | WO 2005/058910 | 6/2005 |

OTHER PUBLICATIONS

Corey et al., 1975, "A Total Synthesis of Natural 20(S)-Campthothecin", Journal of Organic Chemistry, 40 (14), 2140-41.
Henegar at al., 1997, "Practical Asymmetric Synthesis of (S)-4-Ethyl-7,8-dihydo-4-hydroxy-1H-pyrano[3,4-f]indolizine-3,6,10(4H)-trione, a Key Intermediate for the Synthesis of Irinotecan and Other Camptothecin Analogs", Journal of Organic Chemistry, 62, 6588-97.
Kametani et al. 1981, "Studies on the Syntheses of Heterocyclic Compounds, Part 878. Synthesis of (±)-Camptothecin and (±)-10-Methoxycamptothecin via Enamine Annulation", Journal of Chemical Perkin Trans,1 (5), 1563-68.
Wani et al., 1970, "Plants Antitumour Agents: Alkaloids: Synthesis of a Pentacyclin Camptothecin Precursor", Journal of Chemistry Society, Chemical Communications, D, (7) 404.
Wani et al., 1972, "Plant Antitumor Agents, IX. The Total Synthesis of dl-Camptothecin", Journal of the American Chemical Society, 94(10), 3631-32.
Sawada et al., 1991, "Synthesis and Antitumor Activity of 20(S)-Camptothecin Derivatives: Carbamate-Linked, Water Soluble Derivatives of 7-Ethyl-10-hydroxycamptothecin", Chemical and Pharmaceutical Bulletin, vol. 39(6): 1446-1454.
PCT International Search Report for Rao, et al., International App'l No. PCT/IN2005/000326, filed Sep. 27, 2005, Dated Nov. 13, 2007.
Perez, et al., 2001, "Microbiological Resolution of Chiral Arylethyl Carbinols by Nocardia Corallina", Biotechnology Letters, vol. 23(18):1467-1472.
Sakoh, et al., 2004, "Synthesis and Antifungal Activity of Novel 14-Membered Benzomacrolides as Galbonolide Analogues", Chemical & Pharmaceutical Bulletin, vol. 52(1):163-165.

*Primary Examiner*—Brian J Davis
(74) *Attorney, Agent, or Firm*—Law Offices of Albert Wai-Kit Chan, PLLC

(57) ABSTRACT

The present invention discloses a process for efficient production of 2-amino-5-hydroxypropiophenone corresponding to the AB ring part of camptothecin (CPT) skeleton, which is a key intermediate useful for the total synthesis of camptothecin analogs including 7-Ethyl-10-hydroxy camptothecin and novel intermediates thereof.

21 Claims, No Drawings

METHOD OF SYNTHESIZING KEY INTERMEDIATES FOR THE PRODUCTION OF CAMPTOTHECIN DERIVATIVES

RELATED APPLICATIONS

This application is the National Stage of International Application No. PCT/IN2005/000326, filed Sep. 27, 2005 which claims priority of Indian Application No. 1053/CHE/2005, filed Aug. 3, 2005, the entire disclosure of which is incorporated by reference herein in its entirety.

TECHNICAL FIELD

The present invention relates to a process for preparation of 2-amino-5-hydroxypropiophenone, a key intermediate for the synthesis of camptothecin analogs including 7-Ethyl-10-hydroxycamptothecin and novel intermediates thereof.

BACKGROUND AND PRIOR ART

Camptothecin, (herein referred as CPT) a natural alkaloid isolated from the bark of *Camptotheca acuminata* is known to possess antitumor activity by inhibition of nucleic acid synthesis. Due to some severe side effects of this natural compound, various camptothecin derivatives have been synthesized with reduced toxicity and enhanced antitumor activity. One such compound is 7-ethyl-10-[4-(1-piperidino)-1-piperidino]carbonyloxycamptothecin hydrochloride trihydrate (Generic name: irinotecan; herein referred to as CPT-11).

Camptothecin analogs such as CPT-11 and others are derived by a chemical synthesis from CPT, which is obtained from plant sources. However, the amount of CPT obtained from natural plant source is extremely low and the purity of the final CPT-11 is also low (~97%) due to the contamination of related natural products. Further, the demand for CPT-11 is increasing and the supply of CPT is gradually reducing. Several reports have appeared on the total synthesis of CPT and CPT-11, but till recently no synthetic method has been exploited for commercial production.

Various methods for the synthesis of camptothecin and camptothecin analogs are known in the art. These synthetic methods include (i) methods in which naturally occurring camptothecin is synthetically modified to produce a number of analogs and (ii) totally synthetic methods.

U.S. Pat. Nos. 4,604,463; 4,545,880; and 4,473,692 and European patent application No. 0074256 are examples of the former type of synthetic strategy. All these methods require naturally occurring camptothecin, which is difficult to isolate and hence these methods are not suitable for large scale production of camptothecin or analogs.

Examples of total synthetic routes to camptothecin and camptothecin analogs can be found in the following references: J. Org. Chem., 40 (14), 2140-1 (1975); J. Chem. Soc., Perkin Trans 1, (5), 1563-8 (1981); J. Amer. Chem. Soc., 94 (10), 3631-2 (1972); J. Chem. Soc. D, (7), 404 (1970), U.S. Pat. No. 4,031,098, Chem. Pharm. Bull., 39, 1446-54 (1991); J. Org. Chem., 62, 6588-97, (1997).

The best method known till now is to synthesize the two key intermediates (1 and 4) or (3 and 4) and condense by Friedlander reaction to give either CPT or 7-ethyl-10-hydroxycamptothecin (herein referred to as SN-38) via its methyl ether and then converting SN-38 to CPT-11 (Scheme-1)

Scheme 1

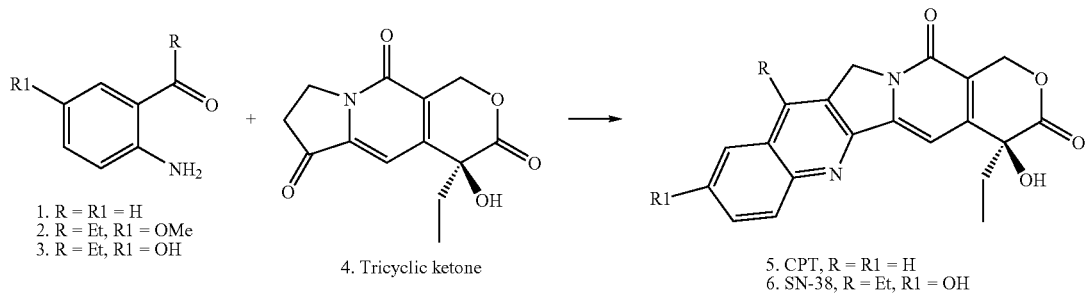

1. R = R1 = H
2. R = Et, R1 = OMe
3. R = Et, R1 = OH

4. Tricyclic ketone

5. CPT, R = R1 = H
6. SN-38, R = Et, R1 = OH

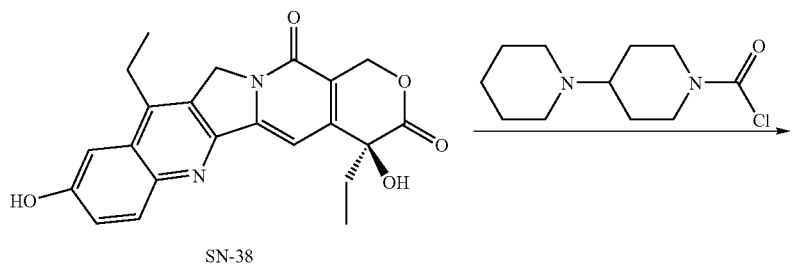

SN-38

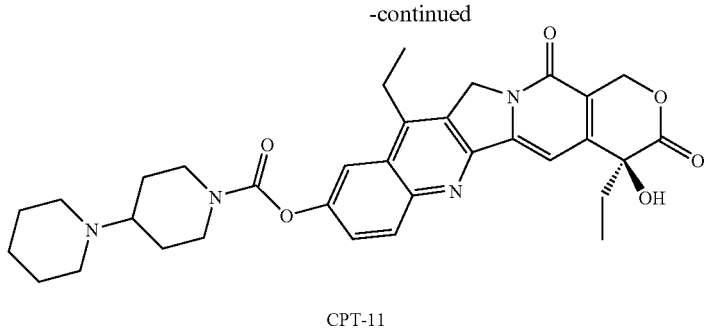

CPT-11

Patent Application no. US2004/0106830 A1 discloses the preparation of AB ring (2-amino-5-hydroxycamptothecin) for CPT-11 synthesis starting from either 5-hydroxy-2-nitrobenzaldehyde or from 5-benzyloxy-2-nitrobenzaldehyde as shown in the scheme 2

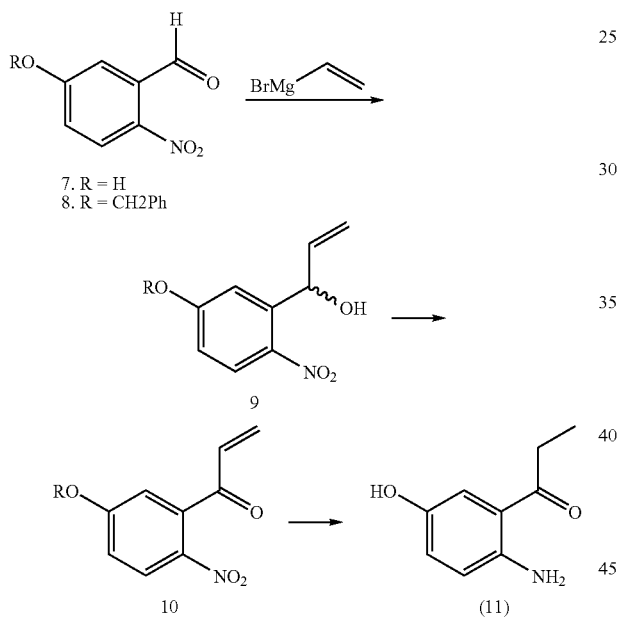

There are several disadvantages in making 2-amino-5-hydroxyprpiophenone from 5-hydroxy-2-nitrobenzaldehyde, which itself is more expensive and involves several steps for its synthesis. In the first step, the Grignard reaction results in substantial formation of byproducts and the isolation of pure compound (9) is tedious. Further, in the final reduction of compound 10, it is difficult to avoid small amounts of 2-amino-5-hydroxypropylbenzene as byproduct, due to the reduction of the carbonyl group.

OBJECTIVES OF THE INVENTION

The objective of the present invention is to provide a suitable method of producing 2-amino-5-hydroxypropiophenone (herein referred to as compound 11) corresponding to AB ring (part of camptothecin from readily available 3-halobenzaldehyde. The reactions are simple to perform and have practical utility.

SUMMARY OF THE INVENTION

The present invention discloses a process for efficient production of 2-amino-5-hydroxypropiophenone corresponding to the AB ring part of camptothecin (CPT) skeleton, which is a key intermediate useful for the total synthesis of camptothecin analogs such as SN-38 and CPT-11.

In one aspect, the present invention discloses a process for preparation of 2-amino-5-hydroxypropiophenone (11) which comprises;

i) reaction of 3-halobenzaldehyde (12), with Grignard reagent under inert atmosphere to give compound (13);

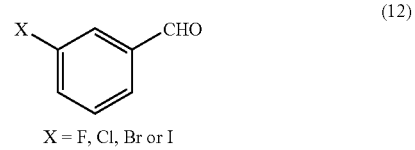

X = F, Cl, Br or I (13)

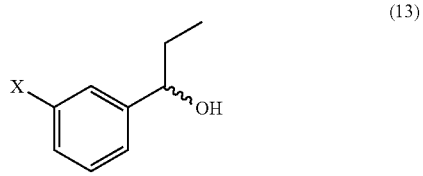

ii) oxidation of the compound (13) to produce compound (14);

(14)

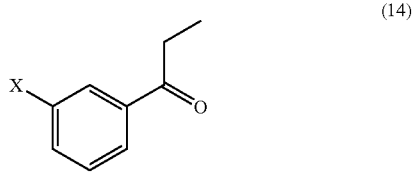

iii) nitration of the compound (14) to obtain compound (15);

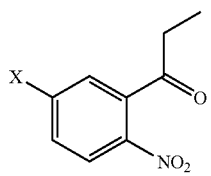

(15)

iv) preparation of compounds (16) from compound (15);

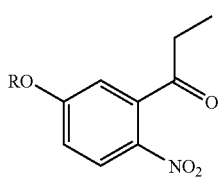

(16)

v) deprotection of the compound (16) to produce compound (17);

(17)

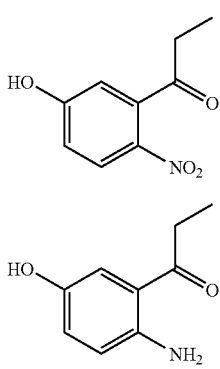

(11)

vi) reduction of the nitro group of compound (17) to obtain compound (11).

2-amino-5-hydroxypropiophenone (11) is used to prepare SN-38 (6) by condensing with (S)-trione (4) under Friedlander condition using acidic medium, which is further converted to Irinotecan (CPT-11). Irinotecan is deesterified in vivo to the active metabolite, 7-ethyl-10-hydroxycamptothecin (SN-38).

DETAILED DESCRIPTION OF INVENTION

According to the present invention, there is a process provided for efficient synthesis of AB ring part of camptothecin or analogs. Thus 2-amino-5-hydroxypropiophenone is made starting from 3-halobenzaldehyde by a simple and commercially feasible approach. The method can be adopted to synthesize 2-amino-5-hydroxy phenyl alkyl ketones. The alkyl group can be 1 to 6 carbons, and if required, can be extended either linear or branched alkyl chain.

As a typical synthetic route, the following scheme describes the present invention.

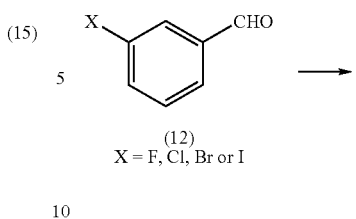

(12)
X = F, Cl, Br or I

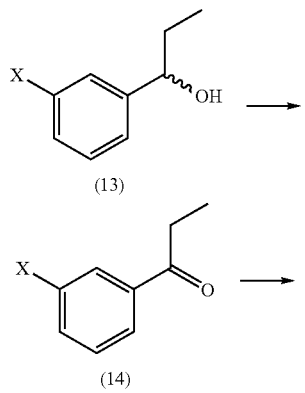

(13)

(14)

(15)

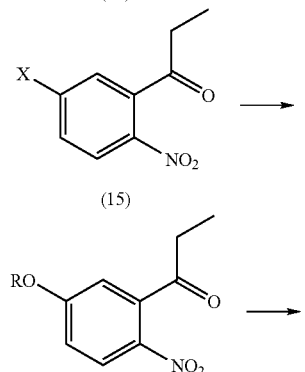

(16)

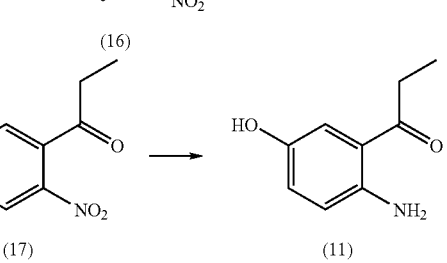

(17)     (11)

In step 1 compound (13) is obtained by reacting a 3-halobenzaldehyde (12) preferably 3-Fluorobenzaldehyde with a Grignard reagent in an inert atmosphere. Ethyl magnesium bromide is preferred. Ethyl magnesium chloride, ethyl magnesium iodide and the like can be equally useful in carrying out this operation. As an inert gas, nitrogen is preferred in view of its cost but any of the noble gasses such as argon, helium etc can be used. The Grignard reagent is prepared by reacting ethyl halide with magnesium in tetrahydrofuran (referred as THF) or solvent ether. The temperature of the reaction is preferably between 0 to 10° C. during the addition and then left at ambient temperature few hours, for completion of reaction. After the reaction, the reaction solution is quenched with saturated aqueous ammonium chloride solution and extracted with a solvent. The solvent is removed to give sufficiently pure alcohol (13) to carry forward for the next reaction.

Compound (13) is oxidized to give 3-halopropiophenone (14). The preferred oxidizing agent is Jones reagent ($Cr_2O_3$/

$H_2SO_4$). Other reagents can also conveniently be used. For example, manganese dioxide; Dess-Martin periodinane; PCC; PDC; DMSO/Oxalylchloride/triethyl amine(Swern oxidation); TEMPO-sodium hypochlorite and the like. Oxidation of (13) is carried out in solvent, preferably acetone. During the oxidation, the temperature of the reaction is maintained between 0 to 10° C. and the Jones reagent in aqueous sulfuric acid is added in acetone to the compound (13) Acetone is removed after the oxidation of (13) completes and the reaction mass is extracted with an organic solvent. The organic layer is washed with water, dried over sodium sulfate and concentrated. As solvent, chloroform, methylene chloride (DCM), ethyl acetate, toluene etc can be used and in particular DCM is preferable. The oxidation reaction takes 2 to 4 hrs to complete.

5-halo-2-nitropropiophenone (15) can be obtained by nitrating 3-halopropiophenone (14) using a nitrating agent. Nitrating agent is selected from nitrating mixture of nitric acid and sulfuric acid or fuming nitric acid. Fuming nitric acid is preferred for nitration. The nitration is carried out with or without solvent. During the nitration, the temperature is controlled by external cooling. The preferred temperature to carry out the nitration reaction is −5° to 5° C. The nitration is completed within 6 to 10 hrs depending upon the batch size. At the end of nitration, the reaction solution is poured over ice or ice/water mixture and stirred to give solid. The nitro compound (15) is extracted with a solvent such as DCM or chloroform and washed with water. The solvent is removed to give the desired nitro compound (15). The compound (15) obtained in the above step is pure enough to carry forward to the next step.

Compound (15) is then converted to a 5-protected or 5-unprotected propiophenone derivative. The protected derivative wherein R is methyl is obtained by treating compound (14) with a suitable alkoxide. Wherein R is methyl, the methanolic solution of a hydroxide is used. Methanolic sodium hydroxide is preferred. Other hydroxides in alcohol can also be used. The above reaction is carried at 0-10° C. for 2 to 5 hrs. After the completion of the reaction, the alkaline medium is acidified to adjust the pH~2-4 with mineral acid and the solvent is removed. The extraction is carried out with a solvent, preferably DCM and organic layer, washed with water. The solvent is removed to give 5-methoxy-2-nitropropiophenone, which is sufficiently pure to take to the next step.

The protected derivative wherein R is ethyl is obtained by treating compound (14) with sodium hydroxide in ethyl alcohol to give 5-ethoxy-2-nitropropiophenone, using similar procedures mentioned above.

Optionally, 5-halo-2-nitropropiophenone (15) can directly be converted to 5-hydroxy-2-nitropropiophenone (17) by heating with inorganic base in aqueous medium.

The 5-alkoxy compound can be smoothly converted to the corresponding phenolic compounds by deprotection on reacting with HBr, HI, Lewis acids, mercaptans, and the like by known procedures and also by heating with metal salts in suitable polar solvent. The said polar solvents are selected from DMF, DSMO, DMA or N-methyl pyrrolidine.

The preferred method of demethylating 5-methoxy-2-nitropropiophenone to give 5-hydroxy-2-nitropropiophenone (17) is by heating with lithium chloride in DMF at reflux temp for 2 to 10 hrs. Deprotection can also be effected with Lewis acids. Thus, the 5-ethoxy compound is deprotected using $ZnCl_2$ in conc. HCl.

Compound (17) is purified by diluting the crude mixture with water and extracting into ethyl acetate and removal of solvent. Isolation of pure 5-hydroxy-2-nitropropiophenone may require use of silica gel column chromatography.

The compound (17) is then converted to 2-amino-5-hydroxypropiophenone (11) by reduction of the nitro group using reducing agent. The compound (17) can be reduced using various reducing agents including hydrogenation in presence of any suitable catalyst such as Raney nickel or Pd/C. The preferred method of reducing compound (17) is by sodium dithionite in alkaline medium. Thus compound (17) is taken in methanol and added to a suspension of sodium dithionate and sodium carbonate in water and the reaction is best carried out at 0 to 30° C. for 2 to 5 hrs to obtain 2-amino-5-hydroxypropiophenone.

The 2-amino-5-hydroxypropiophenone thus obtained is purified by crystallization from suitable organic solvent. Toluene is the preferred solvent for the crystallization of compound. The compound thus obtained is more than 98% pure, by HPLC.

The 2-amino-5-hydroxypropiophenone (11), thus obtained is condensed with cyclic triketone (4) by Friedlander reaction, known in the art, in toluene in presence of acetic acid and p-toluene sulfonic acid to give SN-38. The said reaction is carried out at 100° C. for 15-20 hrs. The solvent is removed, reaction mass taken in acetic acid and diluted with ethanol to provide SN-38 as a colourless compound, having purity greater than 99.5%.

In the following, the invention will become apparent in the course of detailed examples which are given for illustration of the invention and are not intended to be limiting there of.

EXAMPLES

Melting points were taken on MP-96, POLMON and are uncorrected. $^1H$ NMR spectra were determined on a Bruker 300 spectrometer at 300 MHz. Optical rotation were measured on a P-1020, JASCO. Automatic polarimeter using a 1 $cm^{-3}$ capacity quartz cell (10 cm path length). Analytical HPLC analysis were performed on Shimazu system incorporating a model LC-10AT VP pump, a model SPD-M10A VP absorbance detector at 240 nm and a Phenomenex Luna, C-18 column (250×4.6 mm, 5 μm). Column chromatography was performed on silica gel (60-100 mesh) using ethyl acetate in hexane.

Example 1

Preparation of 1-(3-fluorophenyl)propan-1-ol

18 L ethyl bromide were dissolved in 30 L of THF and added dropwise to a suspension of 6 kg of magnesium in 30 L of THF. The reaction solution was next stirred for two hours at 65° to 75° C. and then cooled to 0 to 10° C. 15 kg of 3-fluorobenzaldehyde in 60 L of THF were added while cooling with ice over a period of 6 hr and the reaction solution was stirred overnight at room temp. The reaction solution was quenched with saturated ammonium chloride solution at 0°-10° C. The reaction solution was stirred for one hour, organic layer separated and concentrated. The concentrate was extracted with 40 L of DCM and washed with 30 L of 5% HCl solution. The solvent was removed in vacuo. After drying, 20 kg of 1-(3-Fluoro-phenyl)-propan-1-ol were obtained as a brown oil and taken as such to the next step.

¹H NMR (CDCl₃): δ=0.88 (t, 3H, —CH₂—C$\underline{H_3}$), 1.75 (m, 2H, —C$\underline{H_2}$—CH₃), 4.55 (t, 1H, —C$\underline{H}$—O), 6.9-7.4 (m, 4H, ArH)

Example 2

Preparation of 3-fluoropropiophenone 350 ml of Jones reagent was added dropwise to 100 g of 1-(3-fluorophenyl)propan-1-ol in 1 L of acetone at 0 to 10° C., over a period of two hours. The reaction solution was stirred at 0 to 10° C. for additional 1 hour. The solvent was removed in vacuo. The reaction solution was extracted with 400 ml of DCM and organic layer was dried over sodium sulfate. The solvent was removed in vacuo. After drying, 120 g of 3-fluoropropiophenone were obtained as a yellow oil and taken as such to the next step ¹H NMR (CDCl₃): δ=1.3 (t, 3H, —CH₂—C$\underline{H_3}$), 2.95 (q, 2H, CO—C$\underline{H_2}$—CH₃), 7.25 (m, 1H, A$\underline{r}$5-H), 7.43 (m, 1H, Ar-4H), 7.63 (q, 1H, Ar-6H), 7.75 (bd, 1H, Ar-4H)

Example 3

Preparation of 5-fluoro-2-nitropropiophenone

3 L of fuming nitric acid was added dropwise to 1 kg of 3-fluoropropiophenone at −5 to 5° C., over a period of eight hours. The reaction solution was stirred at 0° C. for two hours. The reaction solution was carefully poured on crushed ice and stirred for 1 hour. The cold solution was filtered and the solids obtained were extracted with 6 L of DCM. The organic layer was separated and washed twice with 3 L of 5% NaHCO3 solution each time and the combined DCM extracts were dried over sodium sulfate. The solvent was removed in vacuo. After drying, 775 g (98%) of 5-fluoro-2-nitropropiophenone were obtained as a yellow liquid, taken as such to next step.

¹HNMR (CDCl₃): δ=1.25 (t, 3H, —CH₂—C$\underline{H_3}$), 2.75 (q, 2H, CO—C$\underline{H_2}$—CH₃), 7.06 (m, 1H, Ar H), 7.28 (m, 1H, Ar H), 8.22 (m, 1H, Ar H).

Example 4

Preparation of 5-methoxy-2-nitropropiophenone 5.6 g of sodium hydroxide dissolved in 84 ml methanol were added dropwise to 14 g of 5-fluoro-2-nitropropiophenone in 84 ml of methanol at 0 to 10° C. The reaction solution was stirred at 0 to 10° C. for two hours. The reaction solution was made acidic to pH 4, by addition of conc. HCl. The solvent was removed in vacuo. The reaction solution was extracted with 200 ml of DCM. DCM extract was washed twice with 100 ml of water each time and the combined DCM extracts were dried over sodium sulfate. The solvent was removed in vacuo. After drying, 14 g of 5-methoxy-2-nitropropiophenone was obtained as a brown viscous liquid and taken as such to the next step.

¹H NMR (CDCl₃): δ=1.20 (t, 3H, —CH₂—C$\underline{H_3}$), 2.7 (q, 2H, CO—C$\underline{H_2}$—CH₃), 3.95 (s, 3H, OMe), 6.70 (d, J=2 Hz, 1H, 6Ar—$\underline{H}$), 6.98 (dd, 1H, 4-ArH), 8.15 (d, J=7 Hz, 1H, 3Ar—H).

Example 5

Preparation of 5-hydroxy-2-nitropropiophenone 1.5 kg of 5-methoxy-2-nitropropiophenone in 12 L of DMF were mixed with 1.5 kg of lithium chloride and heated to reflux for five hours. The solvent was removed in vacuo and to the remaining solution, 40 L of 5% HCl was added. The reaction solution was extracted with 20 L of ethyl acetate each time. The combined organic layers were washed with 20 L of brine and 20 L of water each time. The solvent was removed in vacuo. The residue was purified by column chromatography on silica gel, eluting with 30% ethyl acetate/n-hexane. Compound containing fractions were combined and concentrated to give a yellow solid. The compound was crystallized using 2 L of toluene. M.P: 98-100° C.

¹H NMR (CDCl₃): δ=1.20 (t, 3H, —CH₂—C$\underline{H_3}$), 2.76 (q, 2H, CO—C$\underline{H_2}$—CH₃), 6.64 (d, J=2 Hz, 1H, Ar-6H), 6.94 (dd, 1H, Ar-4H), 8.10 (d, J=7 Hz, 1H, Ar-3H).

Example 6

Preparation of 5-ethoxy-2-nitropropiophenone from 5-fluoro-2-nitropropiophenone 2 g of sodium hydroxide dissolved in 40 ml ethanol were added dropwise to 5 g of 5-fluoro-2-nitropropiophenone in 20 ml of ethanol at 0 to 10° C. The reaction solution was stirred at 0 to 10° C. for two hours and further stirred overnight at ambient temperature. The reaction solution was made acidic to pH 4, by addition of conc. HCl. The solvent was removed in vacuo. The reaction solution was extracted with 200 ml of DCM. DCM extract was washed twice with 100 ml of water each time and the combined DCM extracts were dried over sodium sulfate. The solvent was removed in vacuo. After drying, 1.7 g of 5-ethoxy-2-nitropropiophenone was obtained as a yellow solid. M.P. 58-61° C.

¹H NMR (CDCl₃): δ=1.21 (t, 3H, CO—CH₂—C$\underline{H_3}$), 1.42 (t, 3H, O—CH₂—C$\underline{H_3}$), 2.75 (q, 2H, CO—C$\underline{H_2}$—CH₃), 4.15 (q, 2H, OC$\underline{H_2}$—CH₃), 6.7 (d, J=2 Hz, 1H, Ar-6H), 6.96 (dd, 1H, Ar-4H), 8.27 (d, J=7 Hz, 1H, Ar-6H).

Example 7

Preparation of 5-hydroxy-2-nitropropiophenone from 5-ethoxy-2-nitropropiophenone 6 g of 5-ethoxy-2-nitropropiophenone, 32 g of zinc chloride and 12 ml of conc HCl were heated to 95-100° C. for 72 hrs. The reaction solution was poured onto 40 ml of ice-cold water and stirred for one hour. The reaction mixture was stirred for 1 hr at 0-5° C. The reaction solution was extracted with 200 ml of ethyl acetate, extract washed twice with 100 ml of water each time and the combined ethyl acetate extracts were dried over sodium sulfate. The solvent was removed in vacuo. After drying, 0.6 g of 5-hydroxy-2-nitropropiophenone was obtained as a yellow solid.

Example 8

Preparation of 2-amino-5-hydroxypropiophenone (11)

240 g of 5-hydroxy-2-nitropropiophenone dissolved in 500 ml of methanol was added dropwise to a mixture of 678 g of sodium carbonate and 1.392 kg of sodium dithionite in 6 L of water at 0 to 10° C. The reaction solution was stirred for three hours at room temp. The reaction mixture was filtered and the solids were dissolved in 5 L of ethyl acetate. The ethyl acetate solution was washed twice with 1 L of water each time. The combined ethyl acetate layers were dried over sodium sulfate. The solvent was removed in vacuo. After drying, 165 g of 2-amino-5-hydroxypropiophenone was obtained as a pale yellow solid.

M.P:147-149° C. ¹H NMR (DMSO): δ=1.04 (t, 3H, —CH₂—CH₃), 2.83 (q, 2H, CO—CH₂—CH₃), 6.58 (d, J=7 Hz, 1H, Ar-3H), 6.78 (dd, 1H, Ar-5H), 7.11 (d, J=2 Hz, 1H, Ar-6H), 8.55 (s, 1H, OH).

We claim:

1. A process for preparing 2-amino-5-hydroxypropiophenone to synthesize camptothecin analogs, wherein compound (13)

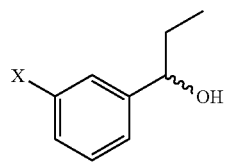

is produced by dropping a Grignard reagent under an inert atmosphere to compound (12)

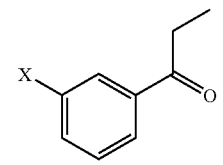

wherein compound (14)

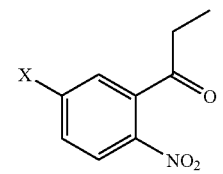

is produced by mixing compound (13) with an oxidizing agent and stirring the mixture in a solvent;
wherein compound (15)

is produced by dropping a nitrating agent to compound (14); wherein compound (16)

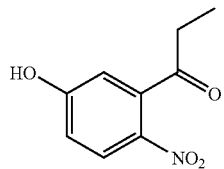

is produced by deprotection of compound (16), or by stirring a mixture of compound (15) and an aqueous base;
wherein compound (11)

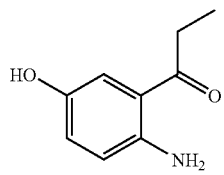

is produced by reduction of compound (17) by mixing with a base and a reducing agent, and stirring the mixture in an aqueous alcoholic solution; and
wherein X is a halogen, and R is hydrogen or a protective group which can be deprotected.

2. The process as claimed in claim 1, wherein the halogen is fluoro and the protective group is a methyl or ethyl group.

3. The process according to claim 1, wherein the Grignard reagent is ethyl magnesium bromide.

4. The process according to claim 1, wherein the oxidizing agent is Jones reagent, active manganese dioxide or TEMPO-sodium hypochlorite.

5. The process according to claim 1, wherein the nitrating agent is fuming nitric acid, or a nitrating mixture of nitric acid and sulfuric acid.

6. The process according to claim 1, wherein the metal hydroxide is sodium hydroxide.

7. The process according to claim 1, wherein the alcohol is methyl alcohol or ethyl alcohol.

8. The process according to claim 1, wherein the deprotection is carried out using a metal salt in polar solvent, or using Lewis acid, when the protective group is methyl.

9. The process according to claim 1, wherein the deprotection is carried out using zinc chloride in an acid, when the protective group is ethyl.

10. The process according to claim 8, wherein the polar solvent is DMF, DMSO, DMA or N-methylpyrrolidine.

11. The process according to claim 9, wherein the acid is hydrochloric acid, when the protective group is ethyl.

12. The process according to claim 1, wherein the reducing agent is sodium dithionite.

13. The process according to claim 1, wherein the base in the last step is sodium carbonate.

14. The process according to claim 1, wherein the aqueous alcoholic solution is aqueous methanolic solution.

15. The process according to claim 4, wherein the oxidizing agent is Jones reagent.

16. The process according to claim 5, wherein the nitrating agent is fuming nitric acid.

17. The process according to claim 8, wherein the metal salt is lithium chloride.

18. The process according to claim 10, wherein the solvent is DMF.

19. A method of preparing a camptothecin analog,

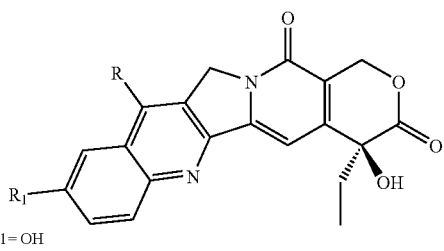

R = Et, R1 = OH comprising the step of reacting 2-amino-5-hydroxypropiophenone, prepared by the process according to claim 1, with a tricyclic ketone,

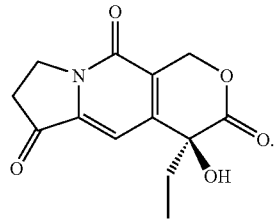

20. 5-Fluoro-2-nitropropiophenone, a novel intermediate for the manufacture of camptothecin, prepared by mixing a nitrating agent with 5-fluoropropiophenone.

21. 5-Alkoxy-2-nitropropiophenone, a novel intermediate for the manufacture of camptothecin, prepared by mixing compound (15),

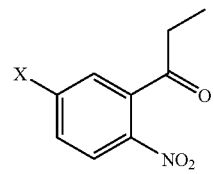

X = halogen, a metal hydroxide and alkanol, and stirring the mixture; wherein alkoxy is methoxy when alkanol is methanol, and alkoxy is ethoxy when alkanol is ethanol.

* * * * *